United States Patent
Liu et al.

(10) Patent No.: US 12,343,448 B2
(45) Date of Patent: Jul. 1, 2025

(54) USE OF STEM CELLS PRODUCED BY STEM CELL GENERATOR IN TREATMENT OF HEMATOPOIETIC DAMAGE

(71) Applicant: EAST CHINA UNIVERSITY OF SCIENCE AND TECHNOLOGY, Shanghai (CN)

(72) Inventors: Changsheng Liu, Shanghai (CN); Kai Dai, Shanghai (CN); Jing Wang, Shanghai (CN); Guilong Li, Shanghai (CN); Qinghao Zhang, Shanghai (CN); Shunshu Deng, Shanghai (CN)

(73) Assignee: EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 895 days.

(21) Appl. No.: 17/427,744

(22) PCT Filed: Jan. 21, 2020

(86) PCT No.: PCT/CN2020/073594
§ 371 (c)(1),
(2) Date: Aug. 2, 2021

(87) PCT Pub. No.: WO2020/156390
PCT Pub. Date: Aug. 6, 2020

(65) Prior Publication Data
US 2022/0040380 A1    Feb. 10, 2022

(30) Foreign Application Priority Data
Jan. 31, 2019 (CN) .......................... 201910099339.4

(51) Int. Cl.
*C12N 5/074*    (2010.01)
*A61L 27/24*    (2006.01)
(Continued)

(52) U.S. Cl.
CPC ........... *A61L 27/3834* (2013.01); *A61L 27/24* (2013.01); *A61L 27/54* (2013.01);
(Continued)

(58) Field of Classification Search
CPC .................................................... C12N 5/0607
See application file for complete search history.

(56) References Cited

U.S. PATENT DOCUMENTS

| 5,197,985 A | 3/1993 | Caplan et al. |
| 5,226,914 A | 7/1993 | Caplan et al. |

(Continued)

FOREIGN PATENT DOCUMENTS

| CN | 1284380 A | 2/2001 |
| CN | 1476903 A | 2/2004 |

(Continued)

OTHER PUBLICATIONS

Domen et al., Regenerative Medicine 2006, Chapter 2, Bone Marrow (Hematopoietic) Stem Cells, https://www.uv.es/~elanuza/Dinamica/Regenerative_Medicine_2006.pdf#page=17, 2006.*

(Continued)

*Primary Examiner* — Rosanne Kosson
(74) *Attorney, Agent, or Firm* — NKL Law; Bin Lu; Allen Xue

(57) ABSTRACT

Disclosed is a stem cell generator for the generation of organoids after the development of biological materials loaded with active substances which are implanted into an animal or a human body. The active substances are mesenchymal stem cells, bone morphogenetic protein-2 or bone morphogenesis protein-7, other growth factors/polypeptides or growth factors/polypeptide combinations having the ability of inducing bone regeneration, or combinations thereof. The stem cell generator contains various types of blood cells and hematopoietic progenitor/stem cells having complete (Continued)

functions. The produced stem cells are used for treating hematopoietic damage, and can treat bone marrow failure and leukemia caused by radiotherapy/chemotherapy.

4 Claims, 11 Drawing Sheets

(51) Int. Cl.
    *A61L 27/38*     (2006.01)
    *A61L 27/54*     (2006.01)

(52) U.S. Cl.
    CPC ... *A61L 2300/252* (2013.01); *A61L 2300/414* (2013.01); *A61L 2430/02* (2013.01)

(56) References Cited

U.S. PATENT DOCUMENTS

| | | | |
|---|---|---|---|
| 7,947,821 | B2 | 5/2011 | Liu et al. |
| 9,593,151 | B2 | 3/2017 | Liu et al. |
| 2007/0071728 | A1 | 3/2007 | Ko et al. |
| 2016/0058867 | A1 | 3/2016 | Kim et al. |
| 2019/0060525 | A1 | 2/2019 | Shah et al. |

FOREIGN PATENT DOCUMENTS

| | | |
|---|---|---|
| CN | 101439204 A | 5/2009 |
| CN | 101564555 A | 10/2009 |
| CN | 1951964 B | 5/2010 |
| CN | 102089426 A | 6/2011 |
| CN | 102973922 A | 3/2013 |
| CN | 101787369 B | 6/2013 |
| CN | 103476440 A | 12/2013 |
| CN | 103495208 A | 1/2014 |
| CN | 103768656 A | 5/2014 |
| CN | 104411318 A | 3/2015 |
| CN | 104857503 A | 8/2015 |
| CN | 105636598 A | 6/2016 |
| CN | 106456669 A | 2/2017 |
| CN | 107427537 A | 12/2017 |
| CN | 109072179 A | 12/2018 |
| CN | 109072197 A | 12/2018 |
| KR | 20160109362 A | 9/2016 |
| WO | 2005105169 A1 | 11/2005 |
| WO | 2007015546 A1 | 2/2007 |
| WO | 2010068707 | 6/2010 |

OTHER PUBLICATIONS

Zhang et al., "VEGF and BMP-2 promote bone regeneration by facilitating bone marrow stem cell homing and differentiation," European Cells and Materials, 27:1-12, 2014.*
Sohier et al., "Porous beta tricalcium phosphate scaffolds used as a BMP-2 delivery system for bone engineering," J Biomedical Materials Research Part A 92A(3):1105-1114, 2009.*
Banfi et al., "Bone marrow stromal damage after chemo/radiotherapy: occurrence, consequences and possibilities of treatment," Leukemia and Lymphoma 42(5):863-870, 2001.*
International Search Report mailed Apr. 27, 2020 corresponding to PCT/CN2020/073594 filed Jan. 21, 2020; 5 pages.
Li, Fei et al., "Organoid and its application in cancer research", Chinese Journal of Cell Biology, Apr. 30, 2017, pp. 394-400, vol. 39(4).
Yu, Xiang et al., "Ectopic osteogenesis induced by microspheres of chiston/dextran sulfate/recombinant human bone morphogenetic protein-2", Chin J Orthop Trauma, Jul. 2015, pp. 616-623, vol. 17(7).
Ma, Junxuan et al., "Biomimetic matrix fabricated by LMP-1 gene-transduced MC3T3-E1 cells for bone regeneration", Biofabrication, Nov. 14, 2017, vol. 9.
Gupta, Munish C. et al., "Efficacy of mesenchymal stem cell enriched grafts in an ovine posterolateral lumbar spine model," Spine, Apr. 1, 2007, pp. 720-726, vol. 32(7).
Zhao, Zixuan et al., "Organoids", Nature Reviews Methods Primers, Dec. 1, 2022, vol. 2(94).
Crippa, Stefania et al., "Mesenchymal stromal cells: role in the BM niche and in the support of hematopoietic stem cell transplantation", Hemasphere, Dec. 1, 2018, vol. 2(6).
Escriba, M. J. et al., "New techniques on embryo manipulation," Journal of Reproductive Immunology, May-Jun. 2002, pp. 149-161, vol. 55(1-2).
He, Xiaoning et al., "BMP2 genetically engineered MSCs and EPCs promote vascularized bone regeneration in rat critical-sized calvarial bone defects", PLoS One, Apr. 2, 2013, pp. 1-12, vol. 8., Issue 4, e60473.
The USPTO, Restriction Requirement of counterpart U.S. Appl. No. 17/427,737 mailed on Apr. 5, 2024.
The USPTO, Non-Final office action of counterpart U.S. Appl. No. 17/427,737 mailed on Sep. 9, 2024.
The USPTO, Non-Final office action of counterpart U.S. Appl. No. 17/427,720 mailed on Jul. 16, 2024.

* cited by examiner

USE OF STEM CELLS PRODUCED BY STEM CELL GENERATOR IN TREATMENT OF HEMATOPOIETIC DAMAGE

TECHNICAL FIELD

The invention relates to the crossing filed of material, life and medicine, and relates to use of pluripotent stem cells produced in a novel stem cell generator for treating bone marrow failure, leukemia and other diseases caused by radiotherapy/chemotherapy.

BACKGROUND

The blood system regulates the transportation of substances, maintains the excitability of the tissues, and has the functions of regulation and defense. It is one of the basic systems that constitute the human body and maintain human life activities. Disorders of the blood system can cause serious consequences. There are many factors that cause hematological diseases, such as chemical factors, physical factors, biological factors, etc., which can become the inducement or direct cause of the onset of hematological diseases, so that the incidence of hematological diseases tends to increase year by year.

Hematopoietic stem cell transplantation (HSCT) therapy is aimed at patients with hematopoietic system damage, such as leukemia patients, patients with hematopoietic disorders after receiving chemotherapy and radiotherapy, etc., to infuse healthy hematopoietic stem cells (HSC) to replace the patient's bone marrow that cannot proliferate and rebuild the patient's hematopoiesis and immune system treatments. Many clinical treatment results show that hematopoietic stem cell transplantation has a good effect on the treatment of various malignant hematological diseases, tumors, hematopoietic failure, severe radiation sickness, genetic diseases and other diseases. According to the source of the donor, HSCT can be divided into autologous HSCT and allogeneic HSCT. Autologous HSCT is taken from the patient or a healthy donor; allogeneic HSCT can be divided into allogeneic transplantation and syngeneic transplantation. Although hematopoietic stem cell transplantation therapy has a good therapeutic effect on the above diseases, hematopoietic stem cell transplantation requires complex matching, and the number of stem cells that a single donor can provide is very limited. Moreover, there are risks of graft-versus-host disease and complications such as infection and bleeding. In 1955, Thomas firstly performed bone marrow hematopoietic stem cell transplantation to treat acute myeloid leukemia. Since then, the use of HSCT to treat malignant hematological diseases has gradually gained consensus, and the research on HSCT has also become more deep. For patients with severe damage to the hematopoietic system, hematopoietic stem cell transplantation is still an effective treatment method. Although the great clinical value of hematopoietic stem cells has been recognized, and new progress has been made in the research of hematopoietic stem cells, their clinical application is still greatly restricted. Due to the scarcity of hematopoietic stem cells, it is difficult to achieve effective expansion using traditional engineering methods. In view of the current situation that the incidence of blood system diseases is increasing year by year, the demand for increasing the source of hematopoietic stem cells has also become more urgent.

SUMMARY OF THE INVENTION

The object of the present invention is to provide a stem cell generator.

The first aspect of the present invention provides a stem cell generator, which is formed by implanting a biological material loaded with an active substance into an animal or human body to produce an organoid after development, and the active substance is mesenchymal stem cell, bone morphogenetic protein-2 (BMP-2), bone morphogenetic protein-7 (BMP-7), other growth factor/polypeptide having the ability to induce bone regeneration, a combination of the growth factor/polypeptide, or a combination thereof.

In another preferred example, the biomaterial is one of collagen, gelatin, chitosan, alginic acid, hyaluronic acid, bacterial cellulose, polylactic acid, polyglycolide, polylactide, polyhydroxy fatty acid ester, polycarbonate, polycaprolactone, polyethylene glycol, polyfumaric acid, hydroxyapatite, calcium sulfate, tricalcium phosphate, tetracalcium phosphate, octacalcium phosphate, calcium metaphosphate, magnesium phosphate, pyrophosphate, calcium silicate, bioglass and decalcified bone matrix, or a copolymer/blend composition thereof.

In another preferred example, the mesenchymal stem cell is bone marrow-derived mesenchymal stem cell, adipose-derived mesenchymal stem cell, or mesenchymal stem cell from other sources; other type of cell having osteogenic differentiation ability; a cell assisting mesenchymal stem cell in osteogenic differentiation, such as vascular endothelial cell and the like.

In another preferred example, the organoid contains pluripotent stem cell and bone marrow cell.

In another preferred example, the pluripotent stem cell is hematopoietic stem/progenitor cell (HSC/HPC), mesenchymal stem cells (MSC) or other type of pluripotent stem cell.

In another preferred example, the active substance is mesenchymal stem cell, the number of cells inoculated is $1\times10^5$-$5\times10^8$ cells per 100-150 mm$^3$ of biomaterial.

In another preferred example, the active substance is bone morphogenetic protein-2, bone morphogenetic protein-7, other growth factor/polypeptide having the ability to induce bone regeneration, a combination of the growth factor/polypeptide, or a combination thereof; and the mass ratio of the active substance to the biomaterial is 0.0001-1:1.

In another preferred example, the animal or human body refers to the muscle pocket, muscle space, intra-muscle, subcutis, or dorsal muscle of the abdominal cavity of the animal or human.

The second aspect of the present invention provides a method for enriching bone marrow cells, comprising the following steps:
 (1) implanting a biological material into an animal or human body;
 (2) generating an organoid after development in the body and enriching bone marrow cells,
 wherein the biological material is a biological material loaded with mesenchymal stem cell, bone morphogenetic protein-2, or bone morphogenetic protein-7, other growth factor/polypeptide having the ability to induce bone regeneration, a combination of the growth factor/polypeptide, or a combination thereof.

In another preferred example, the animal or human body refers to the muscle pocket, muscle space, intra-muscle, subcutis, or dorsal muscle of the abdominal cavity of the animal or human.

The third aspect of the present invention provides use of the stem cell generator according to the first aspect in the manufacture of a medicament for the treatment of hematopoietic injury.

In another preferred example, the hematopoietic injury is hematopoietic injury caused by radiotherapy or chemotherapy.

In another preferred example, the treatment is the transplantation of bone marrow cells produced in a stem cell generator. In another preferred example, the bone marrow cell is a form of a single cell suspension made from cells in a stem cell generator.

In another preferred example, the bone marrow cell is derived from organoid (stem cell generator) formed by implanting a biomaterial loaded with a growth factor and/or cell, or a biomaterial with osteoinductive ability into muscle pockets or subcutaneous parts of an animal or human and developing over a period of time.

In another preferred example, the cell used is adipose-derived mesenchymal stem cell, bone marrow-derived mesenchymal stem cell, or other cells with osteogenic differentiation ability, or a combination thereof.

In another preferred example, the cells produced are hematopoietic stem/progenitor cells (HSC/HPC), mesenchymal stem cells (MSC) or other types of pluripotent stem cells.

The fourth aspect of the present invention provides use of the stem cell generator according to the first aspect in the manufacture of a medicament for promoting the recovery of blood cells and hematopoietic progenitor/stem cells after bone marrow failure caused by radiotherapy and chemotherapy.

The fifth aspect of the present invention provides use of the stem cell generator according to the first aspect in the manufacture of a material for bone marrow transplant, a medicament for the treatment of hematopoietic hypofunction, leukopenia, or acute or chronic leukemia.

In another preferred example, the stem cell generator can be used for the following occasions or disease treatment:
(1) for bone marrow transplantation;
(2) promoting the recovery of hematopoietic system after radiotherapy/chemotherapy;
(3) treating blood system abnormalities such as leukemia.

In another preferred example, the bone marrow cell is used before, during, or after radiotherapy or chemotherapy.

In another preferred example, the hematopoietic hypofunction is one caused by radiation or chemotherapy injury drugs or by bone marrow suppression.

The sixth aspect of the present invention provides a method for treating abnormalities of the hematopoietic system, which includes the steps of:
developing a bone-like organ (stem cell generator) in the body from a biological material loaded with an active substance or a biological material with activity itself;
using the stem cell generator to treat abnormalities of the hematopoietic system.

The stem cell generator contains a variety of pluripotent stem cells including hematopoietic stem/progenitor cells, mesenchymal stem cells, etc., and can be used for the treatment of diseases with abnormal hematopoietic cells.

It should be understood that within the scope of the present invention, the above-mentioned each technical feature of the present invention and each technical feature specifically described thereafter (such as the examples) can be combined with each other to form a new or preferred technical solution. Each feature disclosed in the specification can be replaced by any alternative feature that provides the same, equal or similar purpose. Due to space limitations, they will not be repeated one by one.

DETAILED DESCRIPTION

Figure 1:
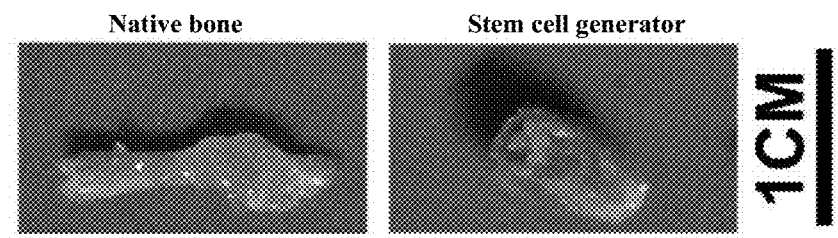
FIG. 1 shows a macroscopic view of the stem cell generator produced by implanting the material I for 6 weeks.

After extensive and intensive researches, the inventors of the present application found that the stem cell generator developed by implanting a biological material loaded with BMP-2 into a body contained fully functional hematopoietic cells and hematopoietic progenitor/stem cells, and also showed that the bone marrow cells contained in the stem cell generator could promote the recovery of hematopoietic hypofunction caused by radiotherapy. After injection of the bone marrow cells through the tail vein, they could promote the recovery of the weight, the number of white blood cells and the red blood cells and platelets of peripheral blood of the mice with hematopoietic injury caused by cobalt-60 irradiation, and the difference is significant compared with the irradiated control group, indicating that the bone marrow cells in the stem cell generator produced by the material loaded with BMP-2 could treat hematopoietic injury. On this basis, the present invention has been completed.

Bone Morphogenetic Protein

Osteogenic active proteins represented by bone morphogenetic protein (BMP) have the effect of inducing ectopic bone formation, and the stem cell generator induced by them contains fully functional bone marrow, and the new bionic bone marrow contains complete hematopoietic precursor cells such as erythroid, myeloid and megakaryocytes. Competitive reconstruction experiments also show that the hematopoietic stem cells in the stem cell generator have long-term reconstitution ability and can rebuild the hematopoietic system of mice irradiated with a lethal dose. It is also found that the content of mesenchymal stem cells in the stem cell generator is much higher than that in the native bone marrow.

Stem Cell Generator

The stem cell generator can be formed by implanting a material loaded with mesenchymal stem cell, bone morphogenetic protein-2, or bone morphogenetic protein-7, other growth factors/polypeptides with the ability to induce bone regeneration, growth factor/polypeptide combinations, or a combination thereof, and then developing in the body, and contains fully functional hematopoietic cells and hematopoietic progenitor/stem cells.

The bone marrow cells contained in the stem cell generator produced by the method of the present invention have the functions of improving the proliferation activity of hematopoietic stem/progenitor cells and promoting the recovery of hematopoietic function and can be used to treat hematopoietic hypofunction due to bone marrow damage caused by radiotherapy, chemotherapy or naturally occurring. Specifically, the hematopoietic microenvironment is one of the prerequisites for the restoration of normal hematopoiesis. The input of bone marrow cells directly improves the hematopoietic microenvironment, promotes the recovery of naturally occurring or induced bone marrow suppression or damaged hematopoietic function, and can stimulate hematopoietic reconstruction after bone marrow transplantation.

The present invention will be further described below in conjunction with specific examples. It should be understood that these examples are only used to illustrate the present invention and not to limit the scope of the present invention. The experimental methods without specific conditions in the following examples generally follow the conventional conditions (such as those described in Sambrook et al., Molecular Cloning: Laboratory Manual (New York: Cold Spring Harbor Laboratory Press, 1989) or the conditions recommended by the manufacturer. Unless stated otherwise, percentages and parts are percentages by weight and parts by weight.

Unless otherwise defined, all professional and scientific terms used herein have the same meaning as those familiar to the skilled in the art. In addition, any methods and materials similar to or equivalent to those described can be applied to the method of the present invention. The preferred implementation methods and materials described herein are for demonstration purposes only.

Example 1 Preparation of Implant Material

Material I: 10 μg of recombinant human bone morphogenetic protein-7 (rhBMP-7) synthesized by eukaryotic or prokaryotic expression system was added to collagen gel (10 mg) and lyophilized to form an active material containing growth factor.

Material II: 5 μg of recombinant human bone morphogenetic protein-2 (rhBMP-2) synthesized by eukaryotic or prokaryotic expression system and $1\times10^6$ mouse mesenchymal stem cells (mMSCs) were added to collagen gel (20 mg) containing tricalcium phosphate (TCP) and lyophilized to form an active material containing growth factor.

Material III: 30 μg of recombinant human bone morphogenetic protein-2 (rhBMP-2) synthesized by eukaryotic or prokaryotic expression system was added to collagen gel (10 mg) and lyophilized to form an active material containing growth factor.

Example 2 Preparation of Bone-Like Organ (Stem Cell Generator)

The material I in Example 1 was implanted into the thigh muscle pocket of an 8-week-old C57BL/6 male mouse. After 6 weeks of feeding, the stem cell generators were taken out. After the muscles attached to the surface were removed, one part of the stem cell generators was placed in a mortar containing a little PBS buffer, crushed with a pestle and then passed through a cell sieve to obtain a single cell suspension. The resulting single cell suspension could be used for flow cytometry detection. Another part was used for taking macro-photographs and making H&E sections.

Example 3 Preparation of Bone-Like Organ (Stem Cell Generator)

The material II in Example 1 was implanted into the thigh muscle pocket of an 8-week-old C57BL/6 male mouse. After 8 weeks of feeding, the stem cell generators were taken out. After the muscles attached to the surface were removed, one part of the stem cell generators was placed in a mortar containing a little PBS buffer, crushed with a pestle and then passed through a cell sieve to obtain a single cell suspension. The resulting single cell suspension could be used for flow cytometry detection. Another part was used for taking macro-photographs and making H&E sections.

Example 4 Preparation of Bone-Like Organ (Stem Cell Generator)

The material III in Example 1 was implanted into the thigh muscle pocket of an 8-week-old C57BL/6 male mouse. After 3 weeks of feeding, the stem cell generators and native bone were taken out. After the muscles attached to the surface were removed, one part of the stem cell generators and native bone were placed in a mortar containing a little PBS buffer, crushed with a pestle and then passed through a cell sieve to obtain a single cell suspension, respectively. 200 μL single cell suspension was used for bone marrow transplantation. Another part was used for taking macro-photographs and making H&E sections.

Example 5

Evaluation of the stem cell generator produced in vivo in Example 2, detection of the number of stem cells contained therein, and conduction of macroscopic and section observations.

The purpose of this example is to evaluate the content of hematopoietic stem cells contained in the stem cell generator produced in the body, and to provide a new source of hematopoietic stem cells for treating tumor patients with hematopoietic hypofunction and bone marrow injury after radiotherapy or chemotherapy and other diseases.

The bone marrow cells in the stem cell generator were in the form of the single cell suspension prepared in Example 2.

Methods: C57BL/6 mice (SPF grade, male, 8 weeks old) were randomly divided into groups. The experiments were grouped as follows

| Group  | Native bone | stem cell generator |
|--------|-------------|---------------------|
| Number | 6           | 6                   |

Figure 2:
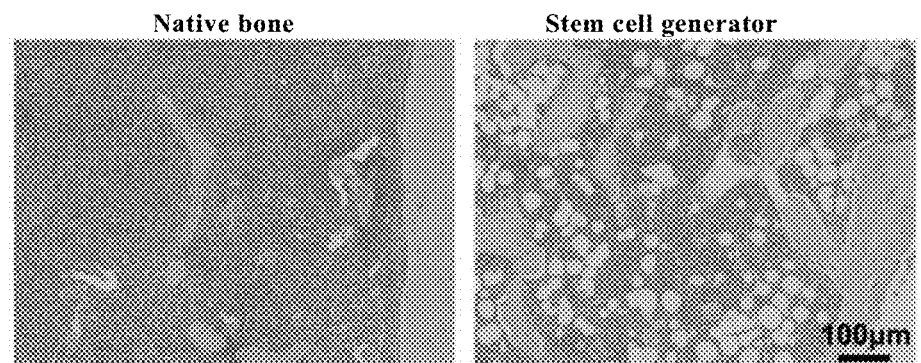
FIG. 2 shows the H&E section of the stem cell generator produced by implanting the material I for 6 weeks.

FIG. 1 showed a digital photo of the stem cell generator produced after 6 weeks of implantation of the material I in Example 1. It could be seen from the figure that the stem cell generator had a deep red color, which implied that it contained a large number of red blood cells and had a bone-like morphology. FIG. 2 showed the H&E section of the stem cell generator. It could be seen that the stem cell generator had a similar microstructure to the native bone and had abundant blood vessels.

Figure 3:
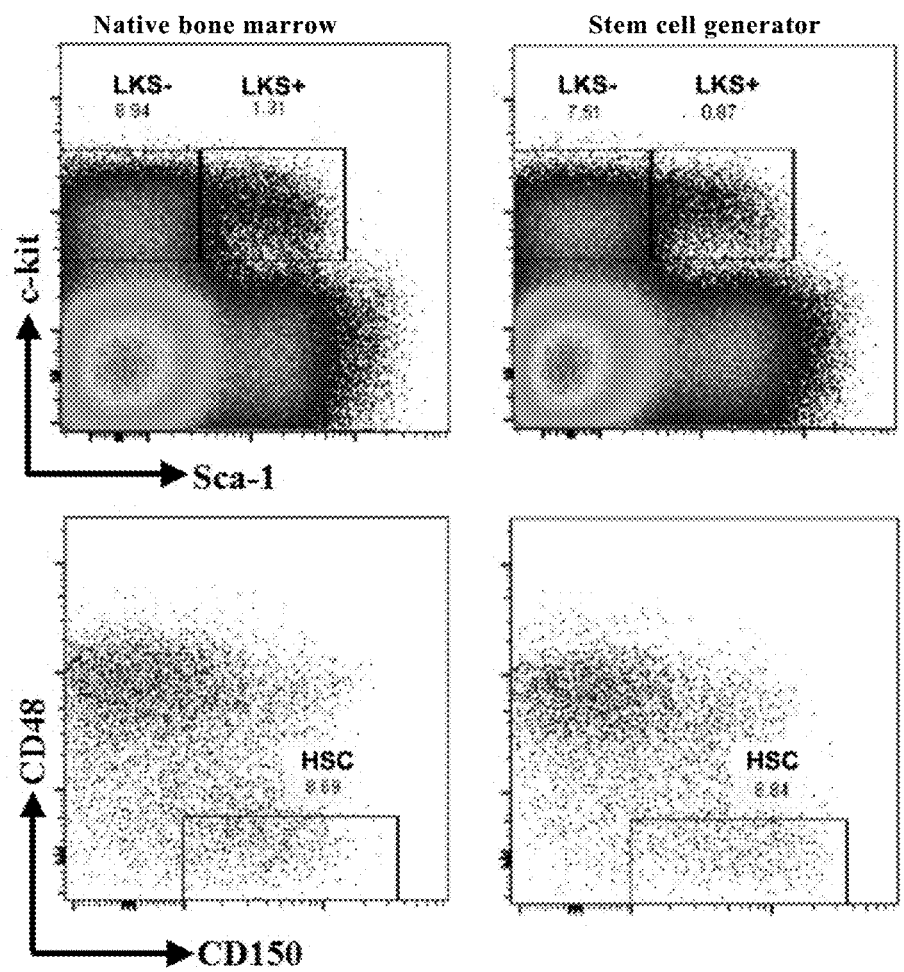
FIG. 3 shows a typical flow cytometric diagram of the stem cell generator produced by implanting the material I for 6 weeks.
Figure 4:
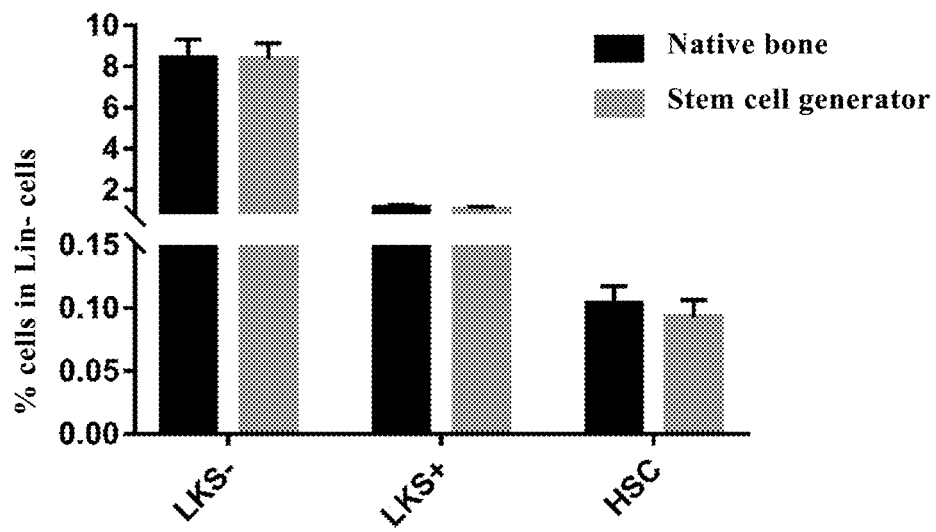
FIG. 4 shows a flow statistic diagram of the stem cell generator produced by implanting the material I for 6 weeks.

FIG. 3 was a typical flow cytometric diagram of the stem cell generator. It could be seen that the stem cell generator had a similar cell composition to the native bone. FIG. 4 was a statistical diagram of the flow cytometric detection of the stem cell generator. It could be seen that there was no significant difference between the proportion of LKS$^-$ cells, LSK$^+$ cells and hematopoietic stem cells (HSCs) contained in the stem cell generator and the proportion of corresponding cells in the native bone marrow.

This example illustrated that the stem cell generator constructed from material I in Example 1 had a structure and function similar to the native bone marrow, and the hematopoietic stem/progenitor cells contained therein had the potential to treat abnormal hematopoietic function.

Example 6

Evaluation of the stem cell generator produced by active material II of Example 1 in vivo, detection of the number of stem cells contained therein, and conduction of macroscopic and section observations.

The purpose of this example is to evaluate the content of hematopoietic stem cells contained in the stem cell generator produced in the body, and to provide a new source of hematopoietic stem cells for treating tumor patients with hematopoietic hypofunction and bone marrow injury after radiotherapy or chemotherapy and other diseases.

The active material used was the scaffold described in material II of Example 1.

The bone marrow cells in the stem cell generator were in the form of the single cell suspension prepared in Example 3.

Methods: C57BL/6 mice (SPF grade, male, 8 weeks old) were randomly divided into groups. The experiments were grouped as follows

| Group  | Native bone | stem cell generator |
|--------|-------------|---------------------|
| Number | 6           | 6                   |

Figure 5:
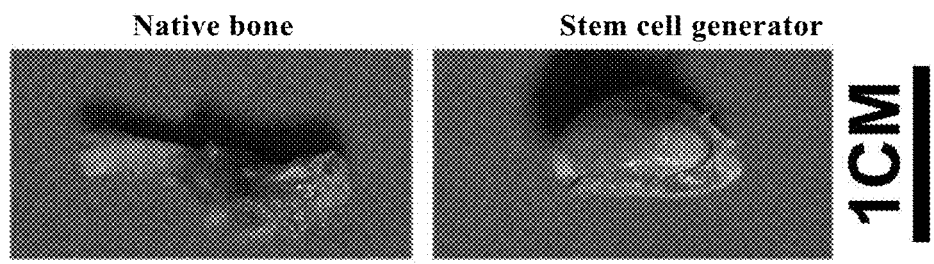
FIG. 5 shows a macroscopic view of the stem cell generator produced by implanting the material II for 8 weeks.
Figure 6:
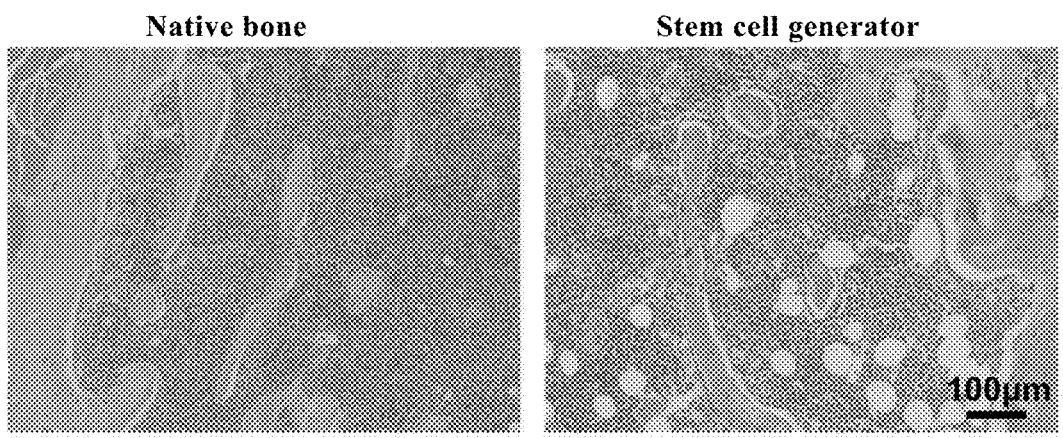
FIG. 6 shows the H&E section of the stem cell generator produced by implanting the material II for 8 weeks.

FIG. 5 showed a digital photo of the stem cell generator produced after 8 weeks of subcutaneous implantation of the material II in Example 1 into the mouse's back. It could be seen from the figure that the stem cell generator was similar in color to the native bone, which implied that it contained a large number of red blood cells and had a bone-like shape. The H&E section of the stem cell generator in FIG. 6 further confirmed that the stem cell generator had the similar microstructure to that of the native bone, had the same cancellous bone and cortical bone structure, and the bone marrow cavity was filled with bone marrow cells and blood vessels.

Figure 7:
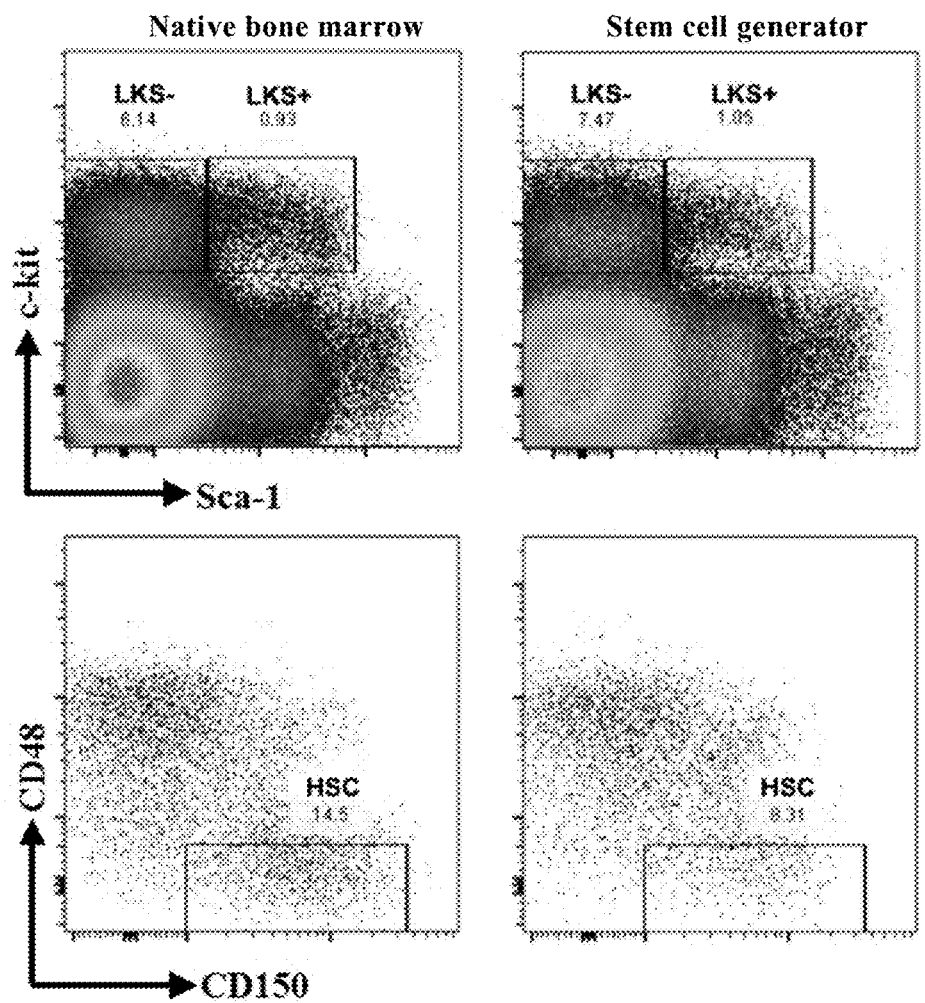
FIG. 7 shows a typical flow cytometric diagram of the stem cell generator produced by implanting the material II for 8 weeks.
Figure 8:
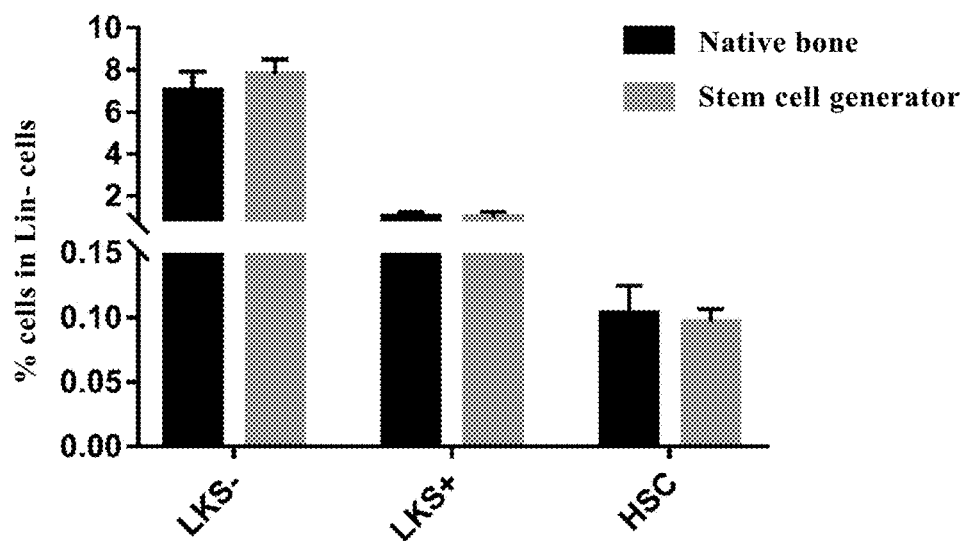
FIG. 8 shows a flow statistic diagram of the stem cell generator produced by implanting the material II for 8 weeks.

FIGS. 7 and 8 showed related flow detection analysis of stem cell generator. It could be seen that the stem cell generator had a similar cell composition to the native bone, and there was no significant difference between the proportion of LKS$^-$ cells, LSK$^+$ cells and hematopoietic stem cells (HSCs) contained in the stem cell generator and the proportion of corresponding cells in the native bone marrow.

This example illustrated that the stem cell generator constructed by material II in Example 1 haD a structure and function similar to the native bone marrow, and the hematopoietic stem/progenitor cells contained therein had the potential to treat abnormal hematopoietic function.

Example 7

The bone marrow cells in the stem cell generator produced in vivo using the active material containing rhBMP-2 described in material III in Example 1 promoted the hematopoietic recovery of the radiation-damaged mice.

The purpose of this example is to evaluate the content of hematopoietic stem cells contained in the stem cell generator produced in the body, and to observe the therapeutic effect of bone marrow cells in the stem cell generator on leukopenia caused by cobalt-60 irradiation, and to look for new treatment method for tumor patients with hematopoietic hypofunction and bone marrow injury after radiotherapy or chemotherapy.

The active material used was the scaffold containing rhBMP-2 described in material III of Example 1.

The bone marrow cells in the stem cell generator were in the form of the single cell suspension prepared in Example 4.

Methods: C57BL/6 mice (SPF grade, female, 8 weeks old) were randomly divided into groups. The experiments were grouped as follows.

| Group | Injection material | Number |
|-------|--------------------|--------|
| normal control + PBS solution transplant group | PBS solution | 10 |
| 6 Gy irradiation + PBS solution transplant group | PBS solution | 5 |

-continued

| Group | | Injection material | Number |
|---|---|---|---|
| 7 Gy irradiation | irradiation + native bone marrow cell transplant group | Native bone marrow suspension | 5 |
| | irradiation + generator cell transplant group | generator bone marrow suspension | 5 |
| | irradiation + PBS solution transplant group | PBS solution | 5 |
| 8 Gy irradiation | irradiation + native bone marrow cell transplant group | Native bone marrow suspension | 5 |
| | irradiation + generator cell transplant group | generator bone marrow suspension | 5 |
| | irradiation + PBS solution transplant group | PBS solution | 5 |
| | irradiation + native bone marrow cell transplant group | Native bone marrow suspension | 5 |
| | irradiation + generator cell transplant group | generator bone marrow suspension | 5 |

Mouse radiotherapy injury model: The mice were subjected to one-time cobalt-60 irradiation according to the irradiation dose given in the grouping table, namely 0 Gy irradiation, 6 Gy irradiation, 7 Gy irradiation, and 8 Gy irradiation.

Intervention treatment: 24 hours after irradiation, the irradiated mice in the corresponding group were given intervention treatment, namely, by injecting 200 μL PBS solution, 200 μL native bone marrow cell suspension, 200 μL stem cell generator cell suspension through tail vein, wherein, native bone marrow cell suspension or stem cell generator cell suspension was the single cell suspension prepared by the method described in Example 4.

Afterwards, the peripheral bloods of each group of mice were collected by sampling orbital bloods at the set sampling point for blood phase detection to observe the treatment effect. The blood test indicators were as follows.

(1) Detecting the number of white blood cells (WBC) in peripheral blood of each group continuously on the $3^{th}$ day, the $6^{th}$ day, . . . (every 3 days, for 30 consecutive days);

(2) Detecting the number of red blood cells (RBC) in peripheral blood of each group continuously on the $3^{th}$ day, the $6^{th}$ day, . . . (every 3 days, for 30 consecutive days);

(3) Detecting the number of platelets (PLT) in peripheral blood of each group continuously on the $3^{th}$ day, the $6^{th}$ day, . . . (every 3 days, for 30 consecutive days);

(4) Detecting the weight of each group continuously on the $3^{th}$ day, the $6^{th}$ day, . . . (every 3 days, for 30 consecutive days).

Figure 9:
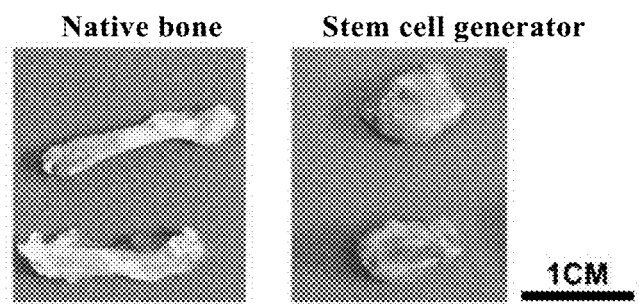
FIG. 9 shows a macroscopic view of the stem cell generator produced by implanting the material III for 3 weeks.
Figure 10:
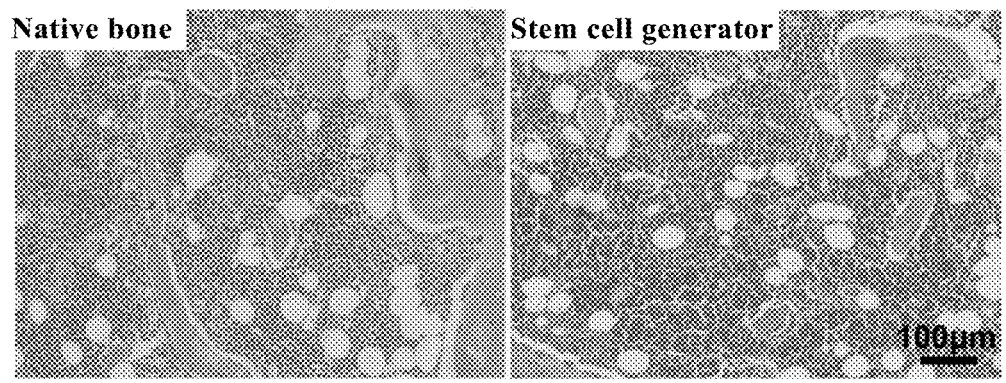
FIG. 10 shows the H&E section of the stem cell generator produced by implanting the material III for 3 weeks.

FIG. 9 showed a digital photo of the stem cell generator 8 weeks after implantation of the material III in Example 1 into muscle pocket. It could be seen that the color of the stem cell generator was similar to that of the native bone, which implied that it contained a large number of red blood cells and had a bone-like morphology, but the volume was bigger than native bone. H&E section of the stem cell generator in FIG. 10 further confirmed that the microstructure of the stem cell generator was similar to that of native bone, and the bone marrow cavity was filled with bone marrow cells and blood vessels.

Figure 11:
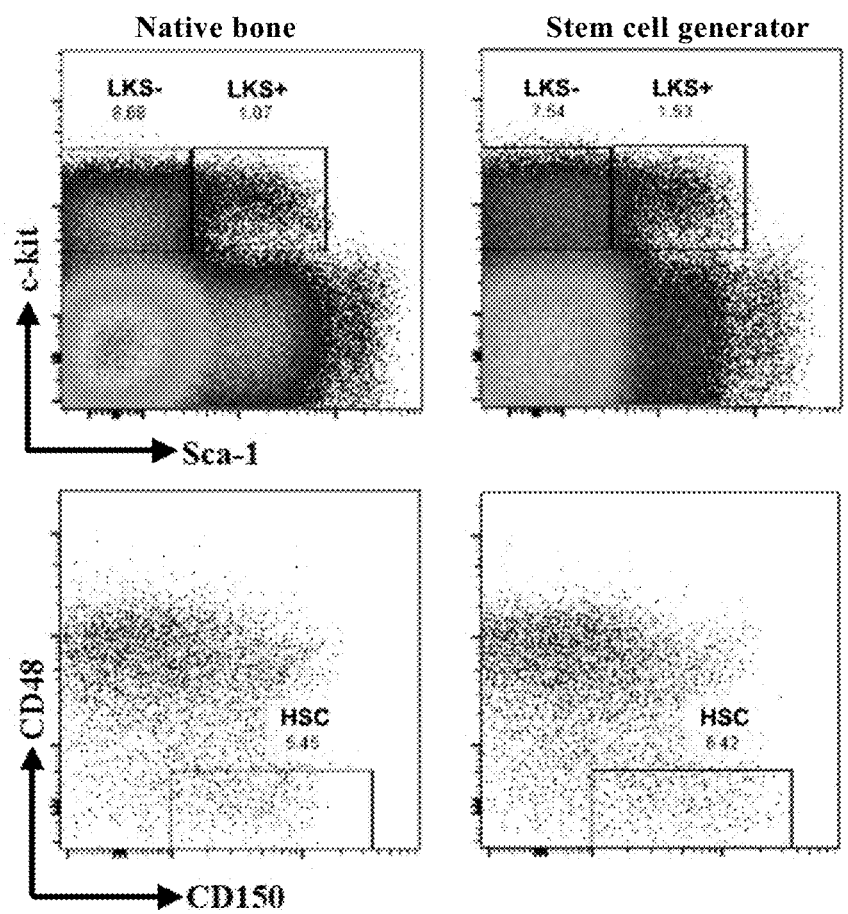
FIG. 11 shows a typical flow cytometric diagram of the stem cell generator produced by implanting the material III for 3 weeks.
Figure 12:
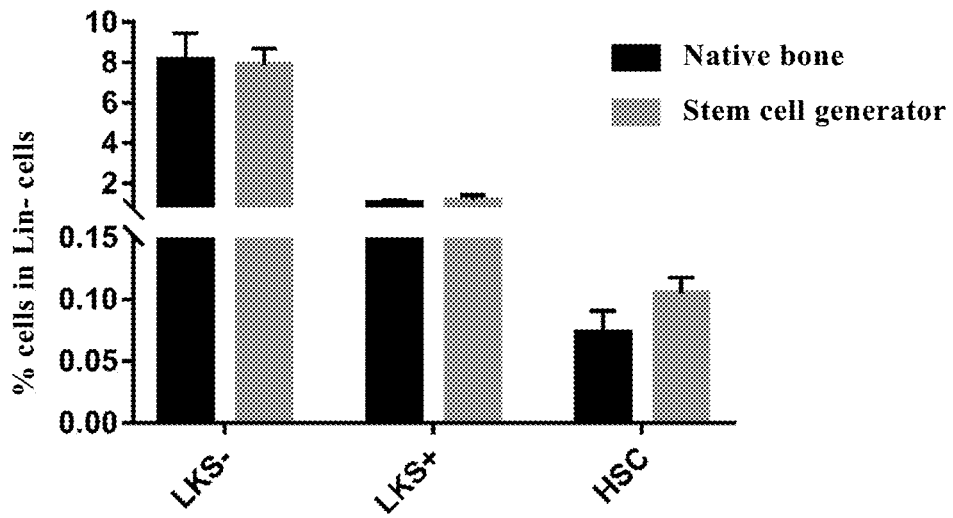
FIG. 12 shows a flow statistic diagram of the stem cell generator produced by implanting the material III for 3 weeks.

FIG. 11 and FIG. 12 showed the flow cytometry correlation analysis of stem cell generator. It could be seen that the stem cell generator and the native bone had similar cell composition, and there was no significant difference between the proportion of LKS− cells, LSK+ cells and hematopoietic stem cells (HSCs) contained in the stem cell generator and the proportion of corresponding cells in the native bone marrow.

The example illustrated that the constructed stem cell generator from the material III in Example 1 had a structure and function similar to native bone marrow, and the hematopoietic stem/progenitor cells contained therein had the potential to treat abnormal hematopoietic function.

In order to further verify the therapeutic effect of the hematopoietic stem cells contained in the stem cell generator on the hematopoietic injury caused by radiotherapy, the mice were subjected to one-time cobalt-60 irradiation according to the irradiation dose given in the grouping table (0 Gy, 6 Gy, 7 Gy, 8 Gy).

Figure 13:
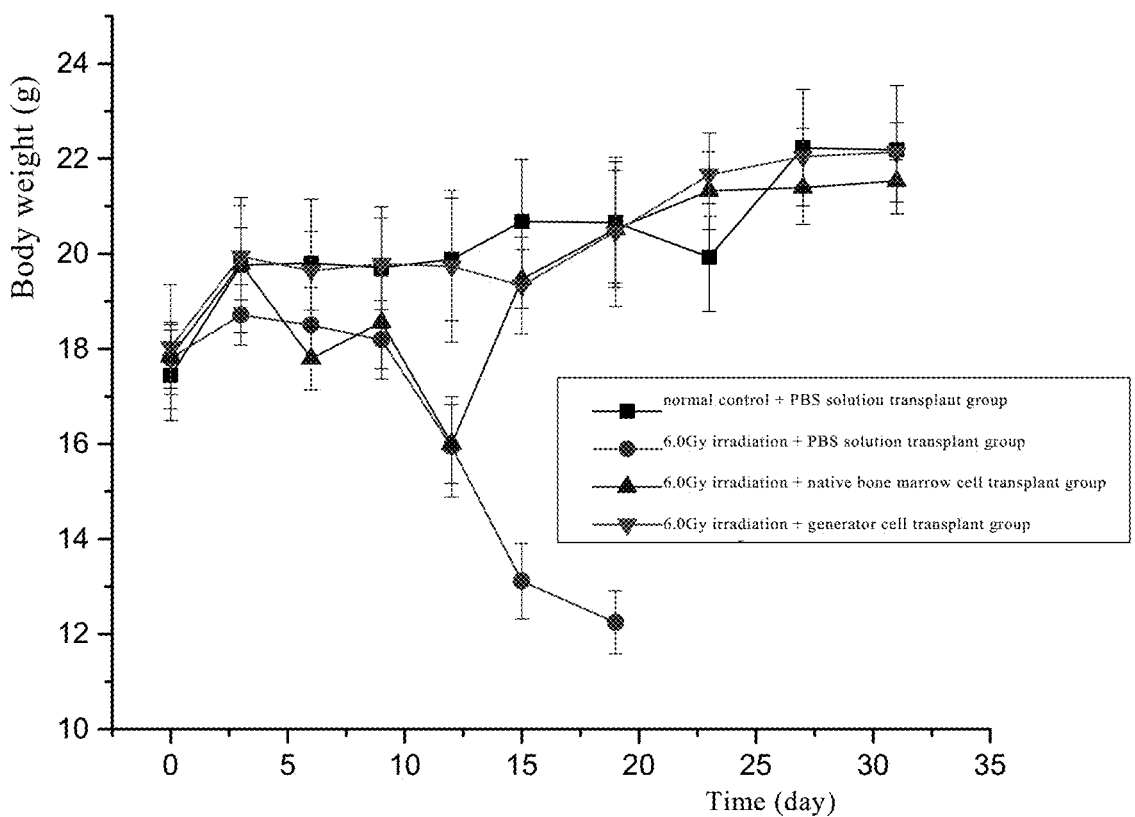
FIG. 13 shows the change in body weight of mice after injection of cells through the tail vein when receiving a 6.0 Gy radiation.
Figure 14:
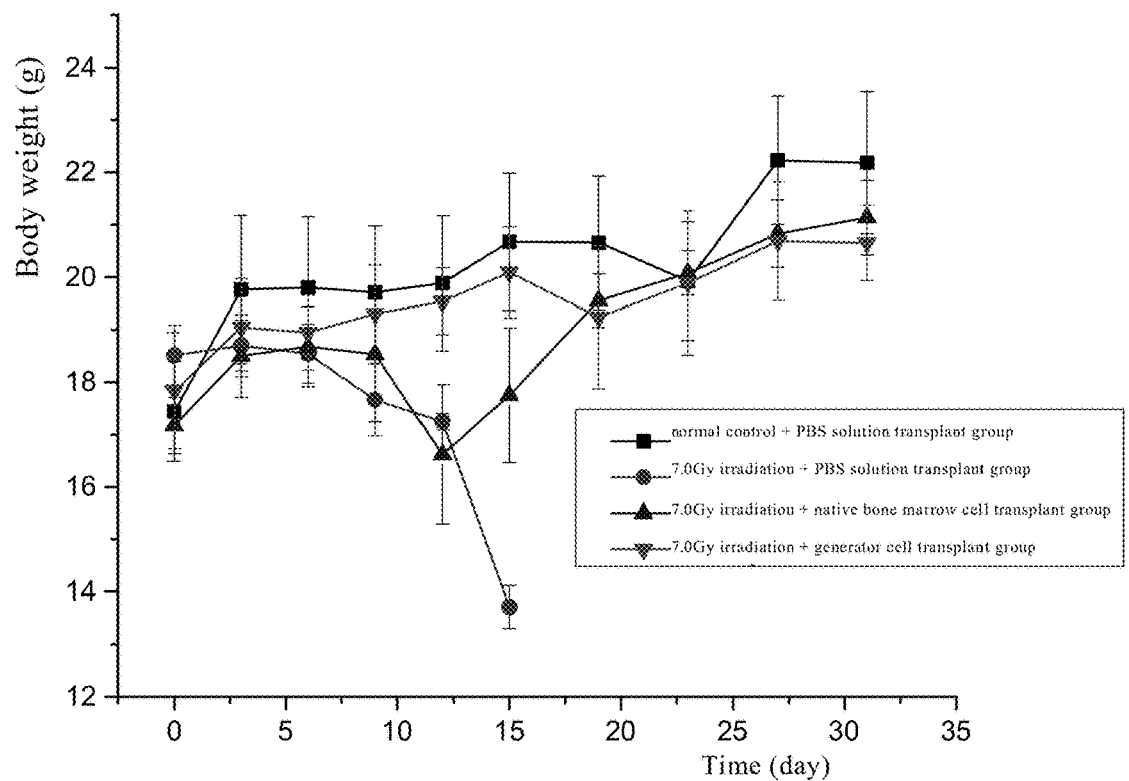
FIG. 14 shows the change in body weight of mice after injection of cells through the tail vein when receiving a 7.0 Gy radiation.
Figure 15:
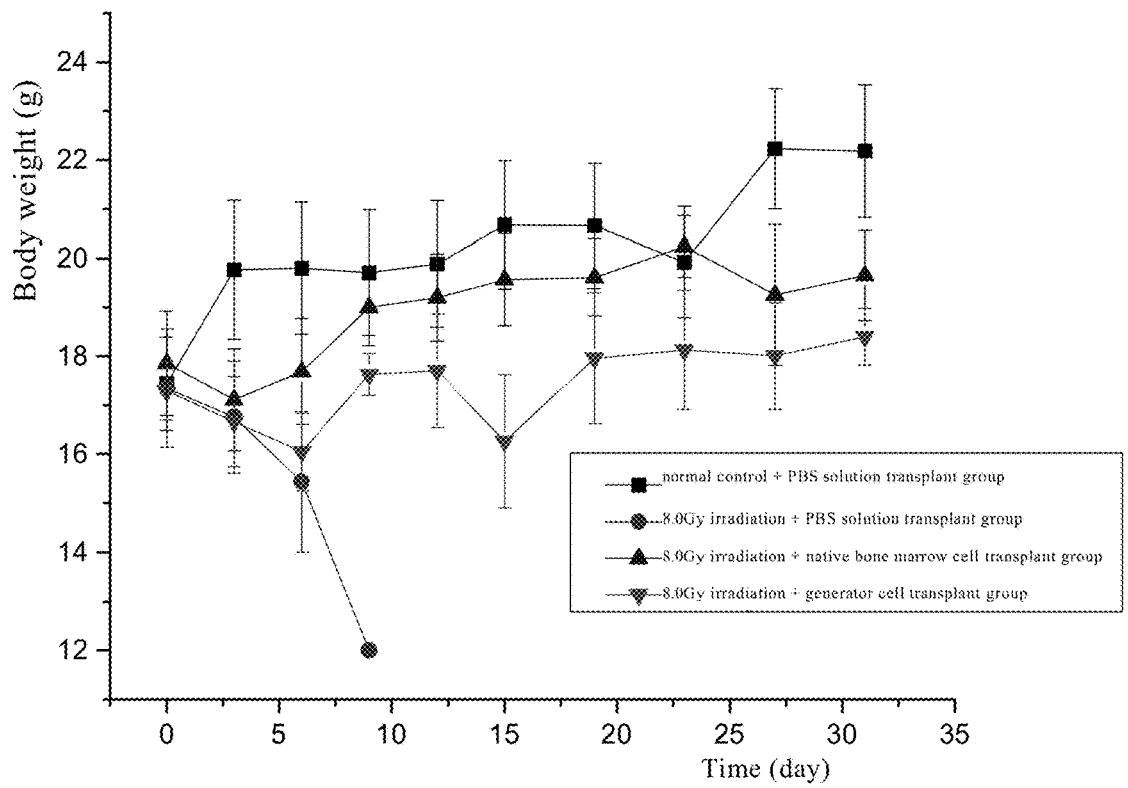
FIG. 15 shows the change in body weight of mice after injection of cells through the tail vein when receiving a 8.0 Gy radiation.

FIGS. 13-15 showed the changes in body weight of the mouse model at different irradiation doses after treatment. The mice were injected with 200 μL of single cell suspension of bone marrow of the same species produced by the stem cell generator through the tail vein immediately after they were irradiated with cobalt 60 (6.0 Gy). FIG. 13 showed that the body weight of the irradiated control group did not change much from 0 to 9 days compared with the normal control group, but decreased sharply after 9 days until death. On the contrary, the weight change of the irradiation treatment group maintained roughly the same change trend as that of the normal control group. The change trends of body weight (7.0 Gy and 8.0 Gy of cobalt 60 irradiation) in FIG. 14 and FIG. 15 were roughly the same as those shown in FIG. 17 and FIG. 18. It was particularly important to point out that due to the excessive radiation dose, the death rate of the irradiated control group had reached 100% within 9 days, and although the treatment group had steadily increased, it still had a gap with the normal control group.

Figure 16:
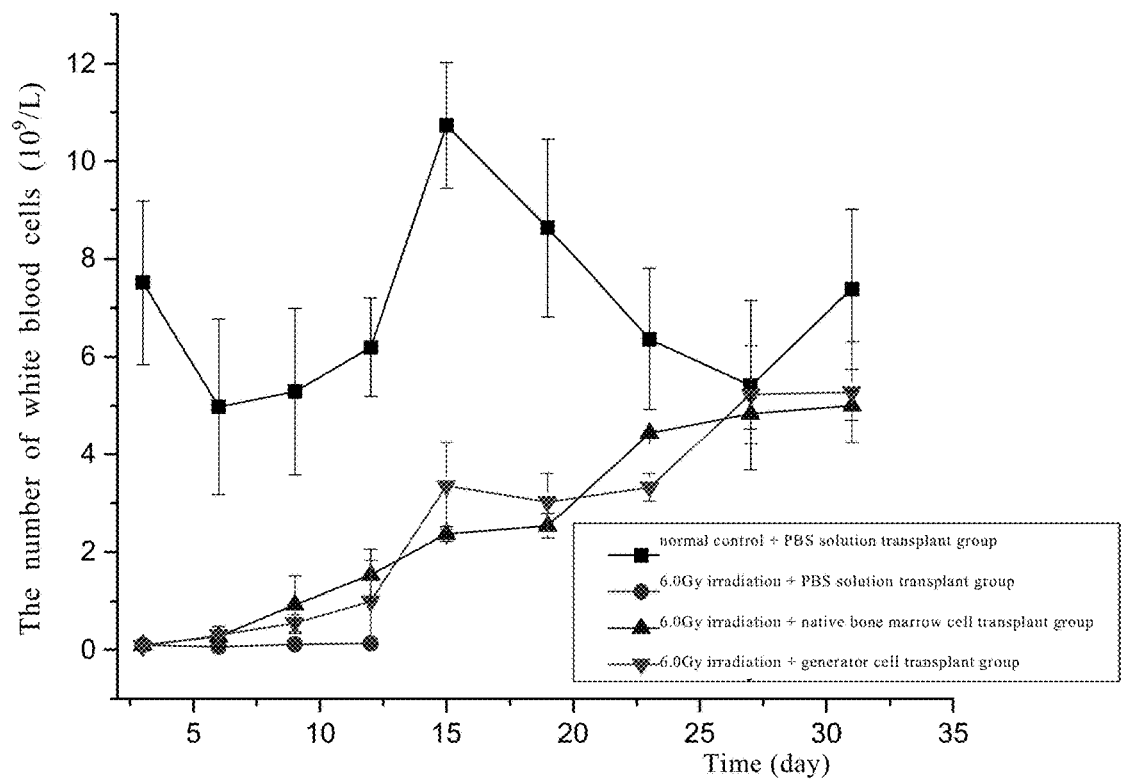
FIG. 16 shows the change in the number of white blood cells in mice after injection of cells through the tail vein when receiving a 6.0 Gy radiation.
Figure 17:
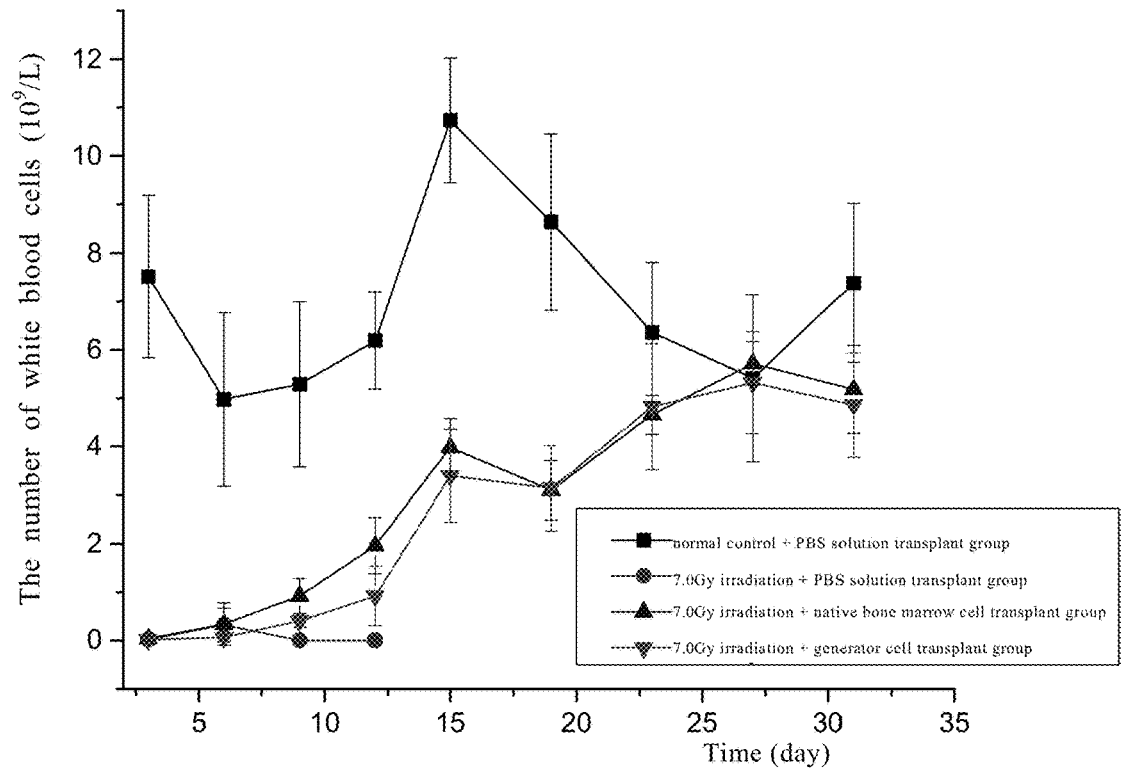
FIG. 17 shows the change in the number of white blood cells in mice after injection of cells through the tail vein when receiving a 7.0 Gy radiation.
Figure 18:
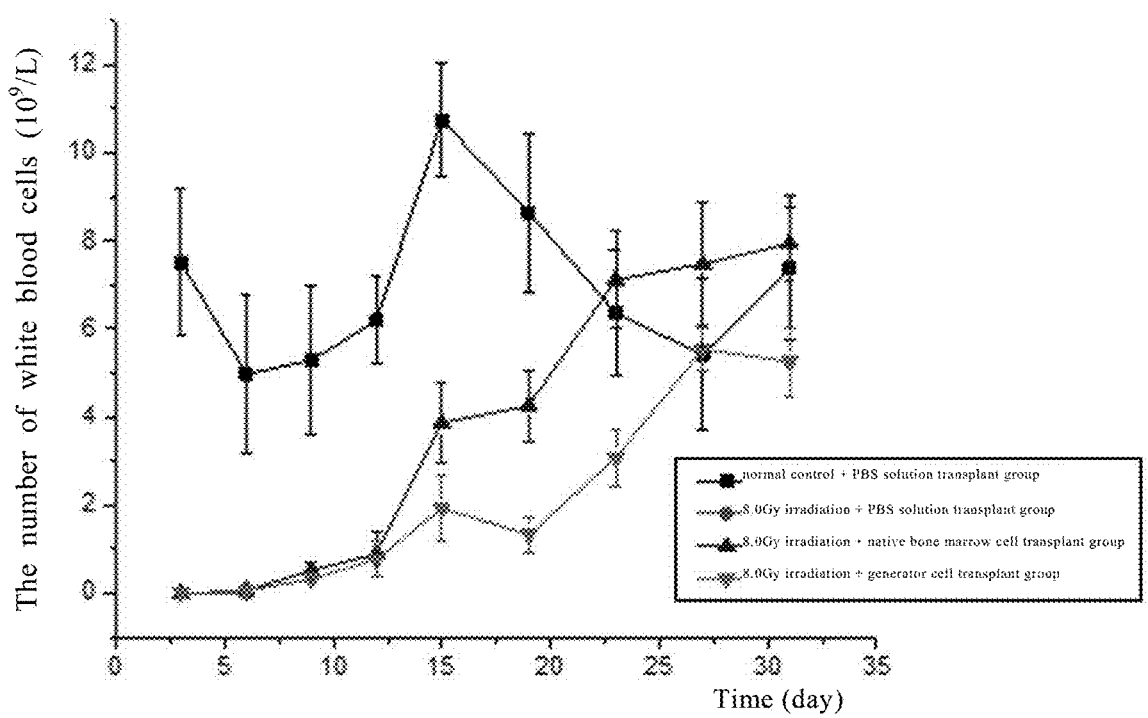
FIG. 18 shows the change in the number of white blood cells in mice after injection of cells through the tail vein when receiving a 8.0 Gy radiation.

FIGS. 16-18 showed the changes in the number of white blood cells in injured mice received different doses of irradiation after treatment. It could be seen from FIG. 16 that the number of white blood cells in the irradiated control group and the treatment group after irradiation dropped sharply to 0, but the number of white blood cells in the treatment group increased steadily over time, and it was equal to the normal control group after 30 days, while the number in irradiated control group was still 0. It showed that after treatment, the hematopoietic function of irradiated mice was restored and the number of white blood cells increases steadily. The change trends of the number of white blood cells in FIGS. 17 and 18 (7.0 Gy and 8.0 Gy of cobalt 60 irradiation) were almost the same as the change trends of body weight in FIGS. 14 and 15.

Figure 19:
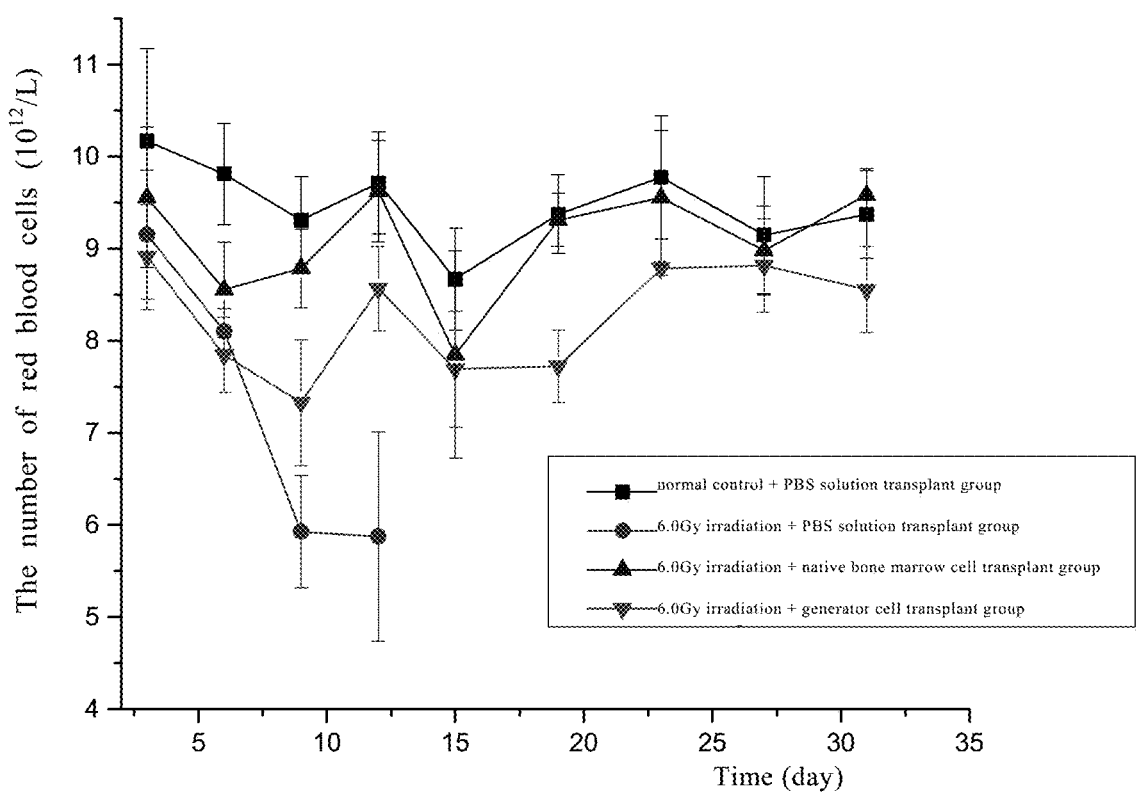
FIG. 19 shows the change in the number of red blood cells in mice after injection of cells through the tail vein when receiving a 6.0 Gy radiation.
Figure 20:
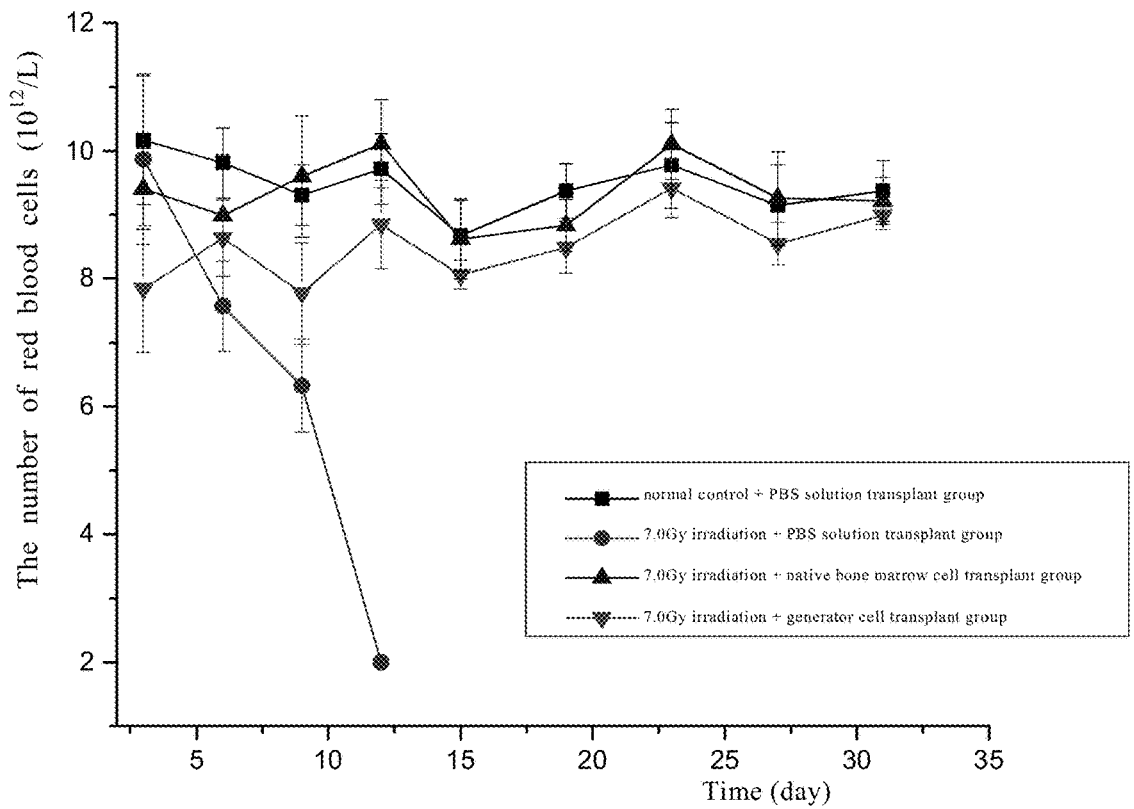
FIG. 20 shows the change in the number of red blood cells in mice after injection of cells through the tail vein when receiving a 7.0 Gy radiation.
Figure 21:
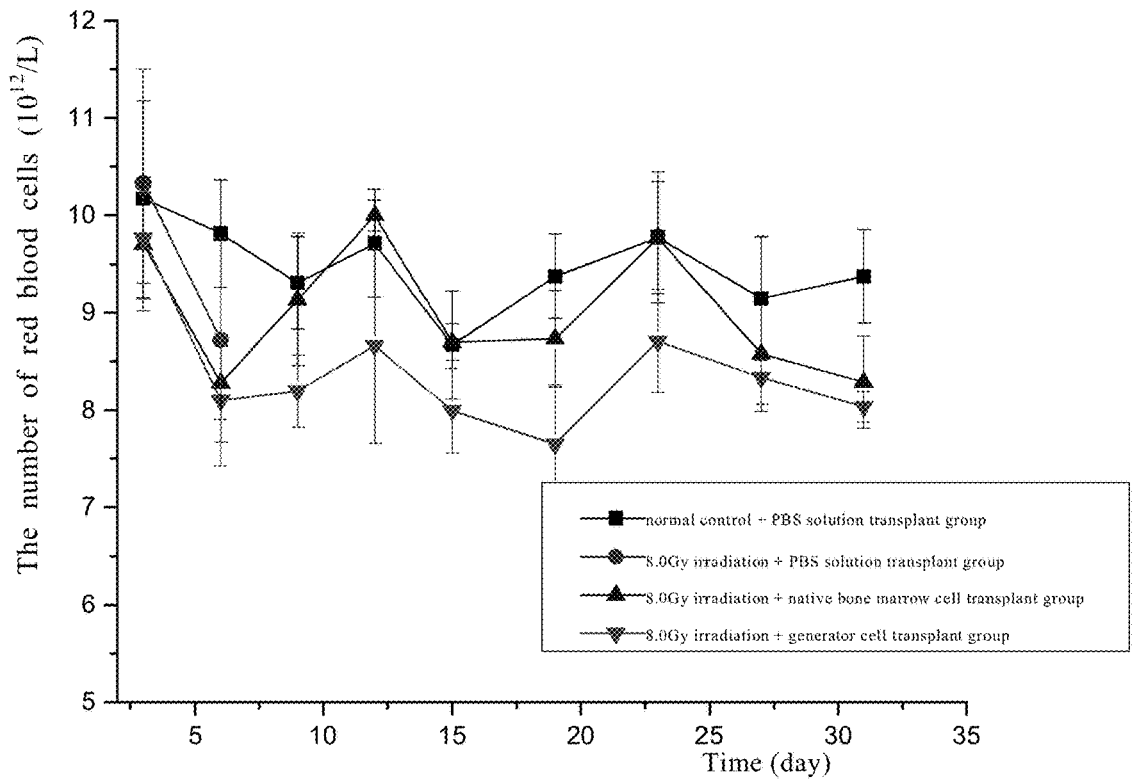
FIG. 21 shows the change in the number of red blood cells in mice after injection of cells through the tail vein when receiving a 8.0 Gy radiation.

FIGS. 19-21 showed the changes in the number of red blood cells in the mouse model received different doses of irradiation after treatment. It could be seen from FIG. 19 that the numbers of red blood cells in the treatment group and the normal control group maintained the same change trend after the tail vein injection treatment after the irradiation, and there was no big numerical difference. The number of red blood cells in the irradiated control group quickly dropped to the lowest value within 9 days, until death. This showed that the injection of bone marrow cell suspension in the bone-like organ (stem cell reactor) in the irradiated group promoted hematopoietic differentiation in the body, restored hematopoietic function, and promoted the number of red blood cells to be roughly the same as the normal group. The change trends of the number of red blood cells in FIGS. 20 and 21 (7.0 Gy and 8.0 Gy of cobalt 60 irradiation) were almost the same as the weight change trend in FIG. 1.

Figure 22:
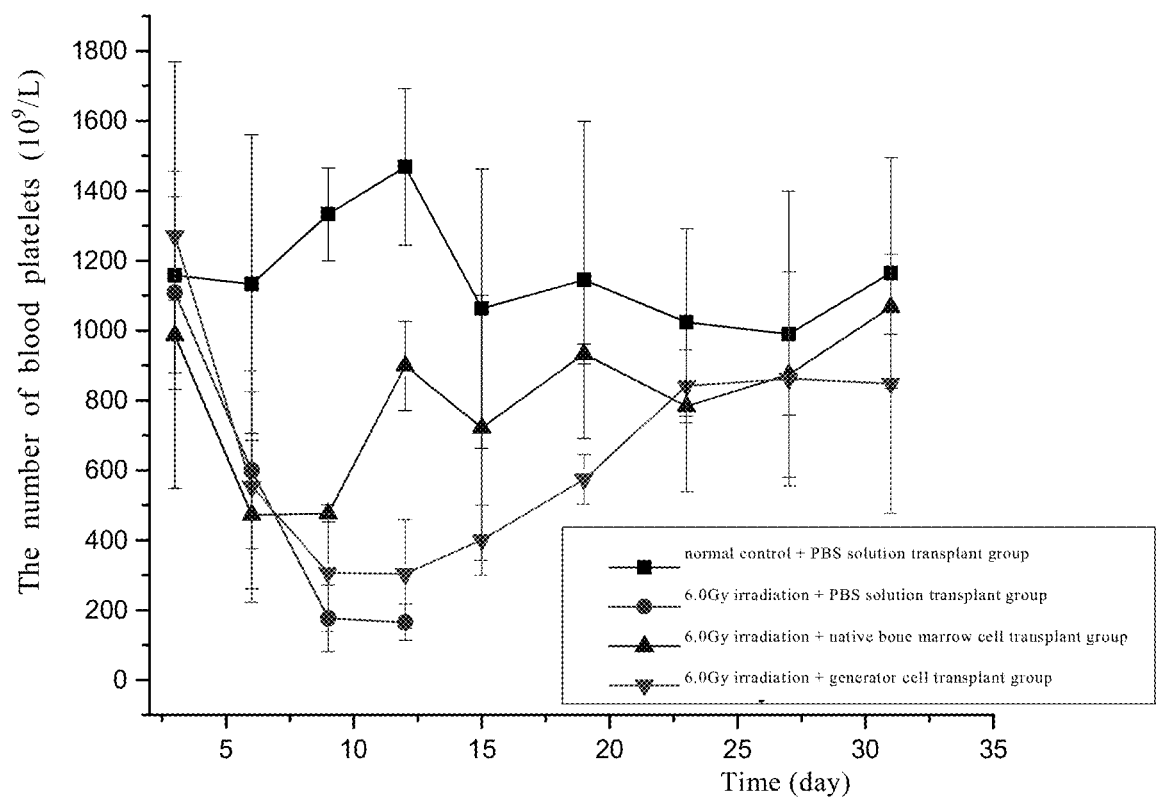
FIG. 22 shows the change in the number of platelets in mice after injection of cells through the tail vein when receiving a 6.0 Gy radiation.
Figure 23:
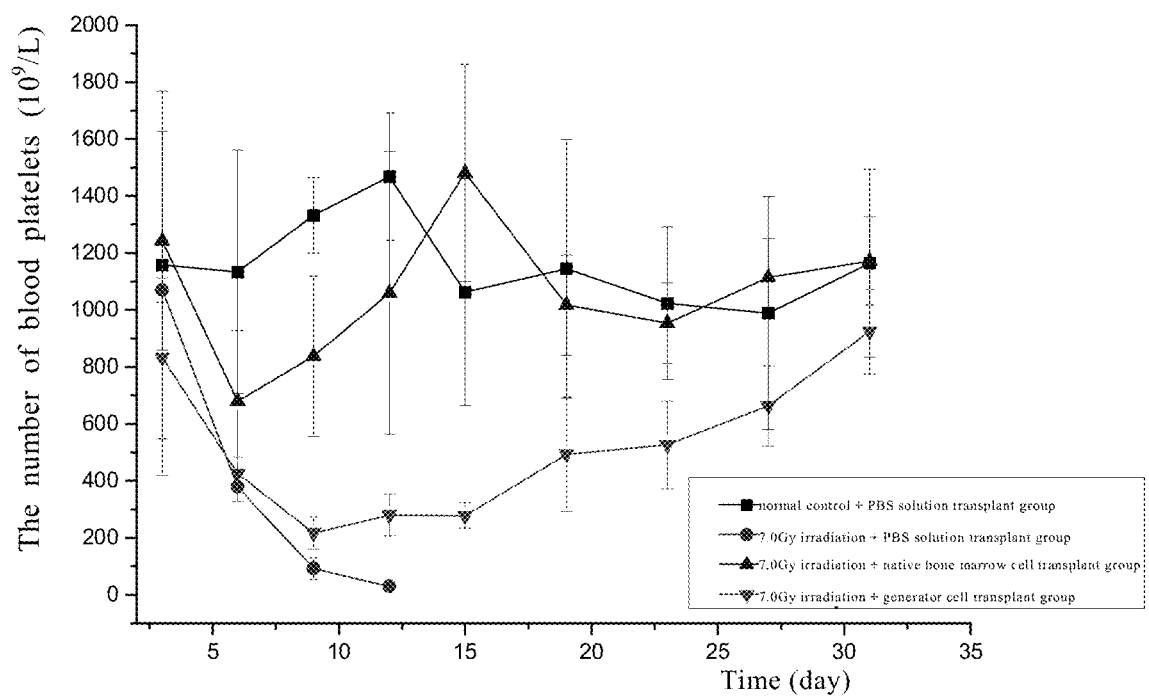
FIG. 23 shows the change in the number of platelets in mice after injection of cells through the tail vein when receiving a 7.0 Gy radiation.
Figure 24:
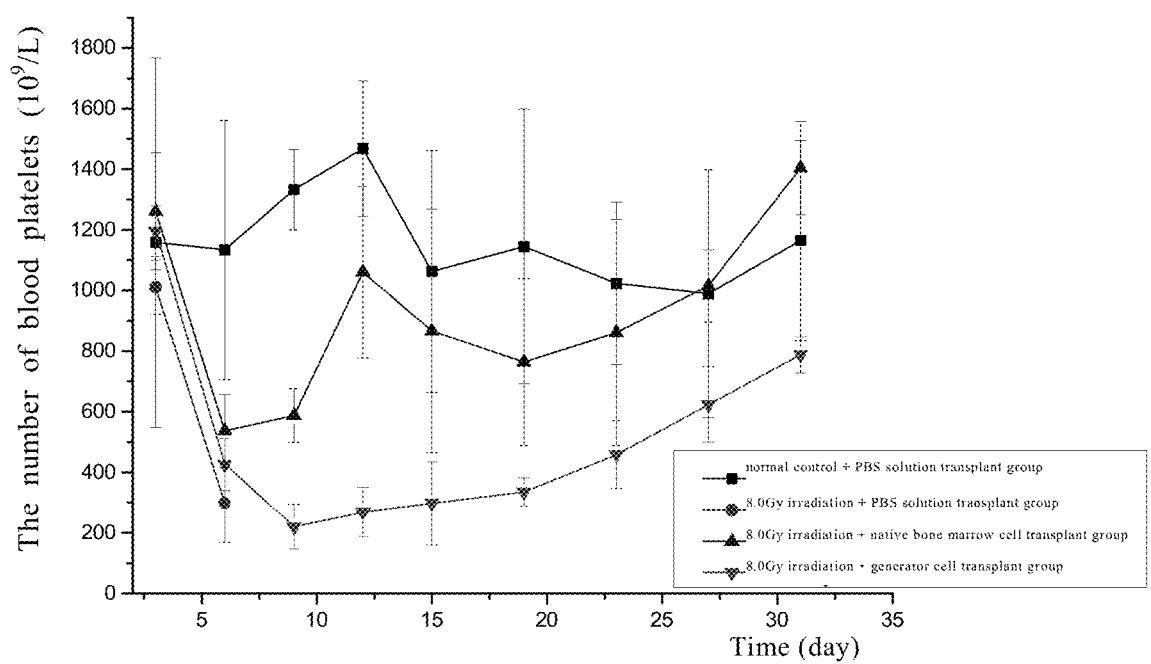
FIG. 24 shows the change in the number of platelets in mice after injection of cells through the tail vein when receiving a 8.0 Gy radiation.

FIGS. 22-24 showed the changes in the number of platelets in the mouse model received different doses of irradiation after treatment. It could be seen from FIG. 22 that both the treatment group and the irradiated control group after irradiation decreased sharply over time, and reached the lowest point at 9 days. After that, the irradiated group remained unchanged until death, while the treatment group increased reversely, and gradually increased over time to the level of the normal control group and restored to the normal level. The obvious difference in FIG. 32 and FIG. 33 was that the recovery degree and speed of radiation treatment group treated by bone marrow cells in the stem cell generator were lower than those of the native bone group, however, the overall trend was the same as that of the normal control group. This was consistent with the weight change trend.

It could be seen that the bone marrow cells in the stem cell generator produced by biomaterial loaded with rhBMP-2 had an effective therapeutic effect on hematopoietic injury caused by radiotherapy and chemotherapy and promoted hematopoiesis. The main effect was that bone marrow cells entered the hematopoietic system and improved the hematopoietic microenvironment, and the various progenitor/stem cells contained therein could normally differentiate into various functions cells to rebuild the blood system.

To sum up, based on the findings of the present invention, it is expected that the stem cell generator of the present invention can be used to treat the hematopoietic hypofunction caused by radiotherapy-caused, chemotherapy-caused or naturally occurring bone marrow injury, accelerate the implantation of bone marrow transplantation, and promote the effective hematopoietic reconstruction. Specifically, stem cell generator can be applied to the following aspects:
1. promoting the recovery of hematopoietic cells when the chemotherapeutic stem cell generator causes hematopoietic hypofunction;
2. promoting the recovery of hematopoietic cells when the radiation injury causes hematopoietic hypofunction;
3. treating leukopenia;
4. treating other abnormalities of the hematopoietic system.

All documents mentioned in the present invention are cited as references in this application, as if each document is individually cited as a reference. In addition, it should be understood that after reading the above teaching content of the present invention, those skilled in the art can make various changes or modifications to the present invention, and these equivalent forms also fall within the scope defined by the appended claims of the present application.

The invention claimed is:

1. A device for the differentiation of stem cells or progenitor cells,
    wherein the device is formed by implanting a biological material loaded with an active substance into an animal or a human body to produce an organoid after development,
    the active substance is bone morphogenetic protein-2 or bone morphogenetic protein-7, and the biological material is collagen, gelatin, chitosan, alginic acid, hyaluronic acid, bacterial cellulose, polylactic acid, polyglycolide, polylactide, polyhydroxy fatty acid ester, polycarbonate, polycaprolactone, polyethylene glycol, polyfumaric acid, or a copolymer/blend composition thereof,
    the weight ratio of the active substance to the biological material is from 0.0001:1 to 1:1, and
    the organoid contains pluripotent stem cells and bone marrow cells.

2. The device of claim 1, wherein the pluripotent stem cells are hematopoietic stem/progenitor cells (HSC/HPC), mesenchymal stem cells (MSC) or another type of pluripotent stem cells.

3. The device of claim 1, wherein implanting into the animal or the human body refers to implanting into a muscle pocket, muscle space, intra-muscle, subcutis, or dorsal muscle of an abdominal cavity of the animal or the human body.

4. The device of claim 1,
    wherein
    the biological material is collagen, gelatin, chitosan, alginic acid, or hyaluronic acid.

* * * * *